(12) United States Patent
Suh et al.

(10) Patent No.: US 12,108,282 B2
(45) Date of Patent: ***Oct. 1, 2024

(54) DEFINING SOURCE OF BITS IN TRIGGER FRAME FOR DISREGARD BITS AND RELEASING REDUNDANT BEAMFORMED BIT

(71) Applicant: HUAWEI TECHNOLOGIES CO., LTD., Shenzhen (CN)

(72) Inventors: Jung Hoon Suh, Ottawa (CA); Yan Xin, Ottawa (CA); Osama Aboul-Magd, Ottawa (CA)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 212 days.

This patent is subject to a terminal disclaimer.

(21) Appl. No.: 17/534,147

(22) Filed: Nov. 23, 2021

(65) Prior Publication Data

US 2022/0182881 A1 Jun. 9, 2022

Related U.S. Application Data

(60) Provisional application No. 63/123,431, filed on Dec. 9, 2020.

(51) Int. Cl.
*H04W 28/06* (2009.01)
*H04W 84/12* (2009.01)

(52) U.S. Cl.
CPC .......... *H04W 28/065* (2013.01); *H04W 84/12* (2013.01)

(58) Field of Classification Search
CPC . H04L 5/0007; H04L 5/0053; H04L 27/2602; H04W 28/065; H04W 72/04; H04W 72/121; H04W 72/1268; H04W 72/23; H04W 72/0453; H04W 74/002; H04W 74/006; H04W 74/06;
(Continued)

(56) References Cited

U.S. PATENT DOCUMENTS 10,708,958 B2 * 7/2020 Ryu .................... H04W 74/085
2016/0227437 A1 * 8/2016 Blanksby .................. H04L 1/00
2016/0323426 A1 * 11/2016 Hedayat ............ H04W 28/0268
(Continued)

FOREIGN PATENT DOCUMENTS

CN 109315013 A 2/2019
CN 111970099 A 11/2020
(Continued)

OTHER PUBLICATIONS

Sameer Vermani et al., IEEE 802.11-20/14641875r23, Proposed Draft Text (PDT-PHY): An Update to Preambles; U-SIG Sep. 14, 2020.
(Continued)

*Primary Examiner* — Frank Duong

(57) ABSTRACT

Methods and systems for transmitting data in a wireless local area network (WLAN) are disclosed. The method comprises transmitting, in the WLAN, a trigger frame from a first wireless communication device, the trigger frame comprising one or more subfields of bits at predefined bit locations within the trigger frame that are populated with values for a second wireless communication device to copy into a trigger based frame for transmission to the first wireless communication device.

20 Claims, 7 Drawing Sheets

(58) Field of Classification Search
CPC . H04W 74/0841; H04W 76/11; H04W 76/15; H04W 84/12
See application file for complete search history.

(56) References Cited

U.S. PATENT DOCUMENTS

| | | | |
|---|---|---|---|
| 2018/0062805 A1 | 3/2018 | Huang et al. | |
| 2019/0124556 A1 | 4/2019 | Verma et al. | |
| 2020/0136884 A1 | 4/2020 | Park et al. | |
| 2020/0245137 A1 | 7/2020 | Chitrakar et al. | |
| 2021/0144752 A1* | 5/2021 | Chen | H04W 84/12 |
| 2021/0227529 A1* | 7/2021 | Chu | H04W 72/23 |
| 2022/0030604 A1* | 1/2022 | Noh | H04W 72/04 |
| 2022/0045889 A1* | 2/2022 | Yu | H04W 72/0453 |
| 2022/0052809 A1* | 2/2022 | Liu | H04L 5/0057 |
| 2022/0095347 A1* | 3/2022 | Huang | H04L 1/0047 |
| 2022/0158786 A1* | 5/2022 | Lim | H04W 76/30 |
| 2023/0198696 A1* | 6/2023 | Huang | H04L 5/0044 370/329 |
| 2023/0276415 A1* | 8/2023 | Ko | H04W 74/06 370/329 |
| 2023/0284041 A1* | 9/2023 | Yu | H04L 5/0044 370/329 |
| 2023/0300803 A1* | 9/2023 | Huang | H04L 5/0037 370/330 |
| 2023/0309151 A1* | 9/2023 | Kim | H04W 28/0908 |
| 2023/0354273 A1* | 11/2023 | Ko | H04L 1/0061 |

FOREIGN PATENT DOCUMENTS

| | | |
|---|---|---|
| WO | 2018144074 A1 | 8/2018 |
| WO | 2018194723 A1 | 10/2018 |
| WO | 2020145890 A1 | 7/2020 |

OTHER PUBLICATIONS

S. Kim and J.-H. Yun, "Wider-Bandwidth Operation of IEEE 802.11 for Extremely High Throughput: Challenges and Solutions for Flexible Puncturing," in IEEE Access, vol. 8; doi: 10.1109/ACCESS. 2020.3040429. 2020.

Evgeny Khorov et al, Current Status and Directions of IEEE 802.11be, the Future Wi-Fi 7, IEEE Access ( vol. 8), 25 pages. May 8, 2020.

11-20/1875r2, "PDT PHY Update to Preamble U-SIG", IEEE 802.11be, Nov. 2020.

11-20/1317r3, "SIG contents discussion for EHT sounding NDP", IEEE 802.11be Nov. 2020.

11-20/566r96," Compendium of straw polls and potential changes to the Specification Framework Document", IEEE 802.11be, Nov. 2020 Nov. 2020.

Steve Shellhammer (QUALCOMM):"Enhanced Trigger Frame for EHT Support", IEEE DRAFT;11-20-1429-03-00BE-Enhanced-Trigger-Framefor-EHT-Sspport, IEEE-SA Mentor, Piscataway, NJ USA, vol. 802.11 EHT; 802.11be, No. 3, Dec. 8, 2020 (Dec. 8, 2020), pp. 1-46, XP068175416.

Steve Shellhammer (QUALCOMM):"Enhanced Trigger Frame for EHT Support", IEEE DRAFT;11-20-1429-02-00BE-Enhanced-Trigger-Frame-For-EHT-Support, IEEE-SA Mentor, Piscataway, NJ USA, vol. 802.11 EHT; 802.11be, No. 2, Oct. 14, 2020 (Oct. 14, 2020), pp. 1-30, XP068173782.

Steve Shellhammer (Qualcomm), Enhanced Trigger Frame for EHT Support, IEEE 802.11-20/1429r3 , IEEE, Dec. 7, 2020, total 13 pages.

Steve Shellhammer (Qualcomm), Enhanced Trigger Frame for EHT Support, IEEE 802.11-20/1429r0 , IEEE, Sep. 2020, total 19 pages.

Sameer Vermani, Proposed Draft Text(PDT-PHY): An update to Preamble, U-SIG,IEEE 802.11-20/1875r2,Nov. 2020, total 14 pages.

\* cited by examiner

DEFINING SOURCE OF BITS IN TRIGGER FRAME FOR DISREGARD BITS AND RELEASING REDUNDANT BEAMFORMED BIT

PRIORITY CLAIM

This application claims priority to U.S. Provisional Patent Application No. 63/123,431, filed Dec. 9, 2020, titled "DEFINING SOURCE OF BITS IN TRIGGER FRAME FOR DISREGARD BITS AND RELEASING REDUNDANT BEAMFORMED BIT," which is herein incorporated by reference.

FIELD

The present application relates to methods and systems for wireless network communications and, more particularly, defining source of bits in a trigger frame for disregard bits and releasing redundant beamformed bit.

BACKGROUND

The Institute of Electrical and Electronics Engineers (IEEE) 802.11™ is a group of media access control (MAC) and physical layer (PHY) specification standards for implementing wireless local area network (WLAN) communication in Wi-Fi frequency bands. The 802.11™ is a family of Wireless LAN working group standards. These standards have experienced steady development and are projected for continued growth to meet the ever-increasing demand for enhanced throughput, reduced latency and jitter, higher reliability, and improved power efficiency driven by new and emerging applications, including virtual or augmented reality, immersive gaming, remote office, and cloud computing.

A new protocol, IEEE 802.11be™, is currently under development by the IEEE 802.11™ Task Group TGbe and will be the next major IEEE 802.11™ amendment to define the next generation of Wi-Fi after IEEE 802.11ax™. IEEE 802.11be™ (also called Extremely High Throughput (EHT)) is expected to support a data rate of at least 30 Gbps and may use a spectrum bandwidth up to 320 MHz for unlicensed operations, double the 160 MHz maximum bandwidth currently contemplated by IEEE 802.11ax. The improved capabilities of the 802.11be may at least in part be attributed to the release of the 6 GHz frequency band for unlicensed use.

Of the elements in 802.11™, the physical layer (PHY) contains a Physical Layer Convergence Procedure (PLCP) sublayer that prepares a well-structured frame allowing a decodable communication between a transmitter and a receiver. The frame, for example, a PLCP protocol data unit (PPDU), consists of multiple fields, including preamble fields and payload. The preamble's content is crucial to synchronize the transmitter with the receiver. The frame informs the receiver of the transmission rate, modulation scheme, and type of error coding to apply, among other information.

To keep transmission overhead to a minimum, it is desirable that the preamble format and content be concise as possible while still permitting flexibility in the conveyed information.

SUMMARY

Example embodiments of the present disclosure define bits of a trigger frame to be copied into bits of the U-SIG of EHT TB PPDU, and to release a redundant bit of the EHT NDP PPDU.

According to a first example aspect is a method for transmitting data in a wireless local area network (WLAN). The method comprises transmitting, in the WLAN, a trigger frame from a first wireless communication device. The trigger frame has one or more subfields of bits at predefined bit locations within the trigger frame. These one or more subfields of bits are populated with values for a second wireless communication device to copy into a trigger based frame for transmission to the first wireless communication device.

In some examples of the first example aspect, the trigger frame includes a common information field and the one or more subfields of bits are included in the common information field.

In some examples of the foregoing aspects, the common information field includes at least 63 bits and the one or more subfields of bits are included in bit locations 53 to 63.

In some examples of the foregoing aspects, the trigger frame includes a user information field, and the one or more subfields of bits are included in the user information field.

In some examples of the foregoing aspects, the one or more subfields of bits are 11 bits included within 5 octets of bits at a beginning of the user information field.

In some examples of the foregoing aspects, the one or more subfields of bits are 11 bits of the user information field. The 11 bits may be contiguous or non-contiguous.

According to a second example aspect, is a method for transmitting data in a wireless local area network (WLAN). The method comprises receiving, by a station (STAs) in the WLAN, a trigger frame. In response to the trigger frame, the method includes copying content from one or more predefined bit locations of the trigger frame into predefined bit locations of the response frame; and transmitting, by the STA, the response frame.

In some examples of the foregoing aspects, the predefined bit locations of the response frame are locations B20 to B25 of a universal signal 1 (U-SIG-1) subfield and B11 to B15 of a universal signal 2 (U-SIG-2) subfield of a universal signal (U-SIG) field of an EHT trigger based (TB) physical layer protocol data unit (PPDU).

In some examples of the foregoing aspects, the one or more predefined bit locations of the trigger frame comprise 11 bits determined from a user info list field of the trigger frame. The 11 bits are 11 contiguous bits.

In some examples of the foregoing aspects, the one or more predefined bit locations of the trigger frame comprise 11 bits determined from a user info list field of the trigger frame. The 11 bits are 11 non-contiguous bits.

According to a further example aspect is a method for transmitting an extremely high throughput (EHT) null data packet (NDP) in a wireless local area network (WLAN). The method comprises transmitting an NDP having an EHT signal field (EHT-SIG) that does not include a beamformed subfield bit.

In some examples of the further aspect, the EHT-SIG field does not comprise any bits for a beamformed subfield and comprises: four bits for a spatial reuse subfield; two bits for a guard interval (GI) and long training field (LTF) subfield; three bits for a number of EHT-LTF symbols subfield; four bits for a number of spatial streams subfield; one bit for a reserved subfield; two bits for a reserved subfield; four bits for a cyclic redundancy check subfield; and six bits for a tail subfield.

In some examples of the further aspect, the EHT-SIG field has four bits for a spatial reuse subfield; two bits for a guard interval (GI) and long training field (LTF) subfield; three bits for a number of EHT-LTF symbols subfield; four bits for a number of spatial streams subfield; one bit for a reserved subfield; two bits for a reserved subfield; four bits for a cyclic redundancy check subfield; and six bits for a tail subfield.

Example embodiments of the present disclosure define bits of a trigger frame to be copied into bits of the U-SIG of EHT TB PPDU, and to release a redundant bit of the EHT NDP PPDU.

Example aspect is a network communication device for transmitting data in a wireless local area network (WLAN), the network communication device comprising: a processor and a memory coupled to the processor, the memory tangibly storing thereon executable instructions. When such instructions are executed by the processor, the processor transmits, in the WLAN, a trigger frame from a first wireless communication device, the trigger frame comprising one or more subfields of bits at predefined bit locations within the trigger frame that are populated with values for a second wireless communication device to copy into a trigger based frame for transmission to the first wireless communication device.

In some examples of the first previous aspect, the trigger frame includes a common information field and the one or more subfields of bits are included in the common information field.

In some examples of the foregoing aspects, the common information field includes at least 63 bits and the one or more subfields of bits are included in bit locations 53 to 63.

In some examples of the foregoing aspects, the trigger frame includes a user information field, and the one or more subfields of bits are included in the user information field.

In some examples of the foregoing aspects, the one or more subfields of bits are 11 bits included within 5 octets of bits at a beginning of the user information field.

In some examples of the foregoing aspects, the one or more subfields of bits are 11 bits of the user information field. The 11 bits may be contiguous or non-contiguous.

According to an example aspect is a network communication device for transmitting data in a wireless local area network (WLAN). The network communication device comprises a processor and a memory coupled to the processor, the memory tangibly storing thereon executable instructions. When the instructions are executed by the processor, the processor receives, by a station (STAs) in the WLAN, a trigger frame. In response to the trigger frame, the processor copies content from one or more predefined bit locations of the trigger frame into predefined bit locations of the response frame, and transmits, by the STA, the response frame.

In some examples of the foregoing aspects, the predefined bit locations of the response frame are locations B20 to B25 of a universal signal 1 (U-SIG-1) subfield and B11 to B15 of a universal signal 2 (U-SIG-2) subfield of a universal signal (U-SIG) field of an EHT trigger based (TB) physical layer protocol data unit (PPDU).

In some examples of the foregoing aspects, the one or more predefined bit locations of the trigger frame comprise 11 bits determined from a user info list field of the trigger frame. The 11 bits are 11 contiguous bits.

In some examples of the foregoing aspects, the one or more predefined bit locations of the trigger frame comprise 11 bits determined from a user info list field of the trigger frame. The 11 bits are 11 non-contiguous bits.

According to a further example aspect is a network communication device for transmitting an extremely high throughput (EHT) null data packet (NDP) in a wireless local area network (WLAN). The network communication device comprises a processor and a memory coupled to the processor, the memory tangibly storing thereon executable instructions. The instructions when executed by the processor, cause the processor to transmit an NDP having an EHT signal field (EHT-SIG) that does not include a beamformed subfield bit.

In some examples of the further aspect, the EHT-SIG field does not comprise any bits for a beamformed subfield and comprises: four bits for a spatial reuse subfield; two bits for a guard interval (GI) and long training field (LTF) subfield; three bits for a number of EHT-LTF symbols subfield; four bits for a number of spatial streams subfield; one bit for a reserved subfield; two bits for a reserved subfield; four bits for a cyclic redundancy check subfield; and six bits for a tail subfield.

In some examples of the further aspect, the EHT-SIG field has four bits for a spatial reuse subfield; two bits for a guard interval (GI) and long training field (LTF) subfield; three bits for a number of EHT-LTF symbols subfield; four bits for a number of spatial streams subfield; one bit for a reserved subfield; two bits for a reserved subfield; four bits for a cyclic redundancy check subfield; and six bits for a tail subfield.

BRIEF DESCRIPTION OF THE DRAWINGS

Reference will now be made, by way of example, to the accompanying drawings which show example embodiments of the present application, and in which:

FIG. 4 illustrates an example of a trigger frame structure that may be used to define the bits for the disregard bits to copy from;

Similar reference numerals may have been used in different figures to denote similar components.

DESCRIPTION OF EXAMPLE EMBODIMENTS

Figure 1:
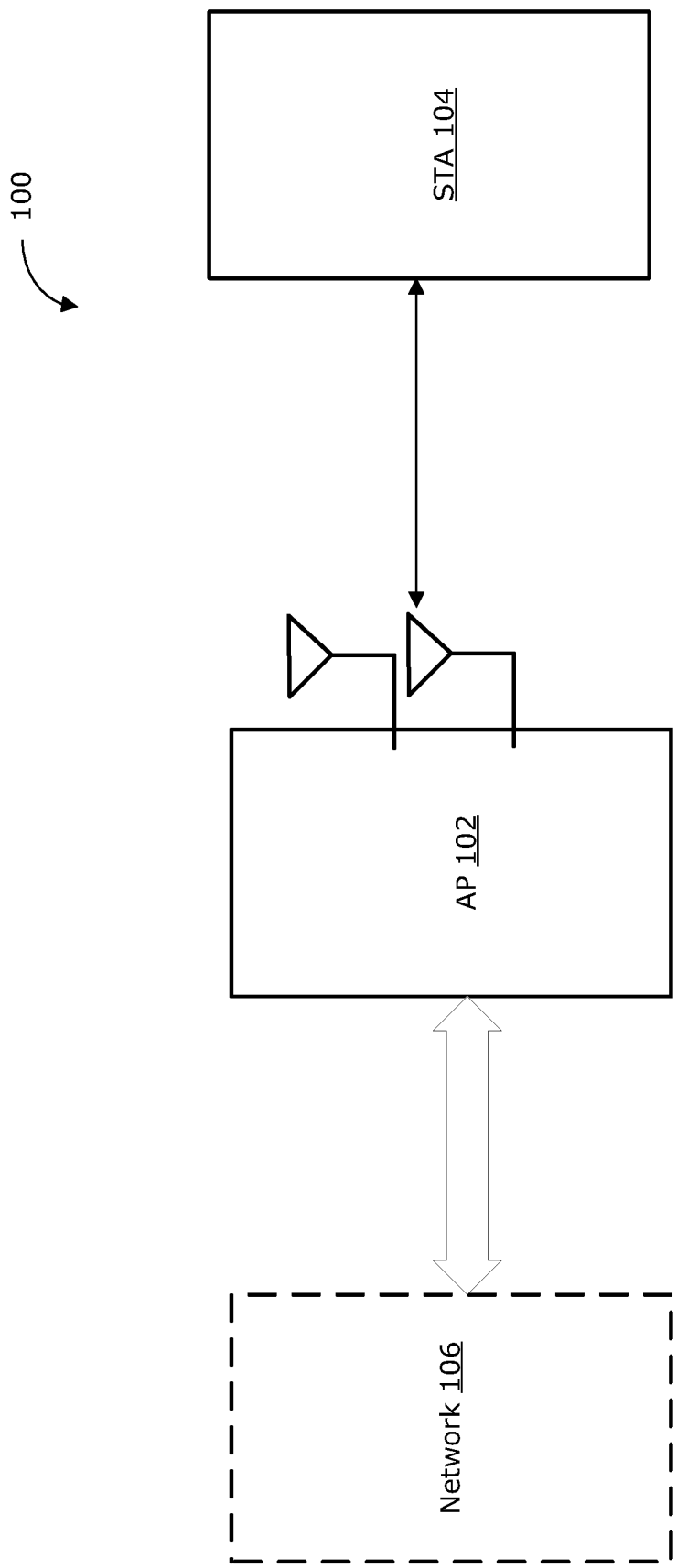
FIG. 1 illustrates an example of a wireless network that includes a plurality of wireless communication apparatuses configured to transmit and receive wireless signals.

For illustrative purposes, specific example embodiments will now be explained in greater detail in conjunction with the figures.

The embodiments set forth herein represent information sufficient to practice the claimed subject matter and illustrate ways of practicing such subject matter. Upon reading the following description in light of the accompanying figures, those of skill in the art will understand the concepts of the claimed subject matter and will recognize applications of these concepts not particularly addressed herein. It should be understood that these concepts and applications fall within the scope of the disclosure and the accompanying claims.

Moreover, it will be appreciated that any module, component, or device disclosed herein that executes instructions may include or otherwise have access to a non-transitory computer/processor-readable storage medium or media for storage of information, such as computer/processor-readable instructions, data structures, program modules, and/or other data. A non-exhaustive list of examples of non-transitory computer/processor-readable storage media includes magnetic cassettes, magnetic tape, magnetic disk storage or other magnetic storage devices, optical disks such as compact disc read-only memory (CD-ROM), digital video discs or digital versatile discs (i.e. DVDs), Blu-ray Disc™, or other optical storage, volatile and non-volatile, removable and non-removable media implemented in any method or technology, random-access memory (RAM), read-only memory (ROM), electrically erasable programmable read-only memory (EEPROM), flash memory or other memory technology. Any such non-transitory computer/processor storage media may be part of a device or accessible or connectable thereto. Computer/processor readable/executable instructions to implement an application or module described herein may be stored or otherwise held by such non-transitory computer/processor readable storage media.

The following is a partial list of acronyms and associated definitions that may be used in the following description:

EHT Enhanced High Throughput
SIG Signal field
EHT-SIG EHT-SIG field
U-SIG Universal Signal field
TB Trigger Based
PHY Physical layer
PLCP PHY Convergence Protocol
PPDU PLCP Protocol Data Unit
SS Spatial Stream
NDP Null Data Packet
TF Trigger Frame
BW Bandwidth Among the signal structure formats being developed in respect of IEEE 802.11be™ is an EHT Trigger-Based (TB) PPDU that will be transmitted in response to a trigger frame (TF). For the EHT Trigger-Based (TB) PPDU, an EHT Universal Signal (U-SIG) preamble field has been proposed. In existing proposals, the EHT U-SIG field includes Disregard subfields that are to be populated with data copied from the TF. According to one example aspect, the present disclosure provides a TF format that specifies the data that is to be copied from the TF to the Disregard subfields of the EHT U-SIG field of the EHT TB PPDU.

Another signal structure format being developed in respect of IEEE 802.11be™ is an EHT Null Data Packet (NDP) PPDU that is used for channel sounding. The EHT NDP PPDU may also include an EHT U-SIG field in its preamble. Further, a beamformed bit subfield has been proposed for inclusion in such the EHT U-SIG field. Such a bit is not required because the EHT NDP PPDU will not require a subfield for a beamformed bit. According to a further example aspect, the present disclosure provides an EHT NDP PPDU format that enables an EHT U-SIG field that does not include a beamformed bit.

Accordingly, example embodiments define bits of the trigger frame to be copied into disregard bits of the EHT U-SIG of the EHT TB PPDU are described herein. Also, a suitable EHT NDP PPDU frame format is described for conserving resources within the EHT U-SIG field of the EHT NDP PPDU.

FIG. 1 shows a wireless network 100 that includes a plurality of wireless communication devices configured to transmit and receive wireless signals according to example embodiments. The wireless network 100 may be a Wireless Local Area Network (WLAN), although embodiments are not limited as such.

The wireless communication devices include an access point station (AP) 102 and one or more non-access point stations (STAs) 104. In some embodiments, AP 102 and STA 104 may be configured to transmit and receive signals within wireless network 100 in accordance with specific communication standards and/or protocols, such as any of the Institute of Electrical and Electronics Engineers (IEEE) 802.11™ standards including, IEEE 802.11n™, IEEE 802.11ac™, IEEE 802.11ax™ and/or proposed specifications for WLANs such as IEEE 802.11be™. Communication within wireless network 100 may also be suitable to transmit and/or receive communications in accordance with other techniques and standards, including Long-Term Evolution (LTE) standard as promulgated by the Third Generation Partnership Project (3GPP). In further examples, a wireless standard can include a Fifth Generation (5G) wireless standard.

In some examples, the wireless network 100 may be configured for Very High Throughput (VHT) communications in accordance with the IEEE 802.11ac™ standard (referred to as the 11ac standard hereinafter), High Efficiency (HE) communications in accordance with the IEEE 802.11ax™ standard (referred to as the 11ax standard hereinafter), or Extremely High Throughput (EHT) in accordance with the proposed IEEE 802.11be standard (referred to as the 11be standard hereinafter), or any other suitable wireless communication standards between the AP 102 and the STA 104. The wireless network 100 may be configured to employ orthogonal frequency-division multiple access (OFDMA) techniques.

The STA 104 may be associated with the AP 102 through a registration procedure. Upon being associated, AP 102 is able to communicate with STA 104 in the wireless network 100. STA 104 may include any of the following: a desktop computer, a notebook computer, a tablet computer, a smartphone, an Internet-of-Things (IoT) device (e.g., a sensor, a camera, a thermostat, a household appliance, etc.), a wearable device (e.g., a smartwatch, smart eyeglasses, a head-mounted device, etc.), server computers, storage devices, and so forth.

In example embodiments, AP 102 is configured to function as an interface between the STA 104 and a network 106 where AP 102 may forward requests to the network 106 via a bi-directional communication link and pass responses received from network 106 onto STA 104 through a bi-directional wireless channel.

It is to be understood that although a single instance of each AP 102, STA 104, and network 106 is shown, there may be embodiments where multiple instances of each component are present within wireless network 100.

Figure 2:
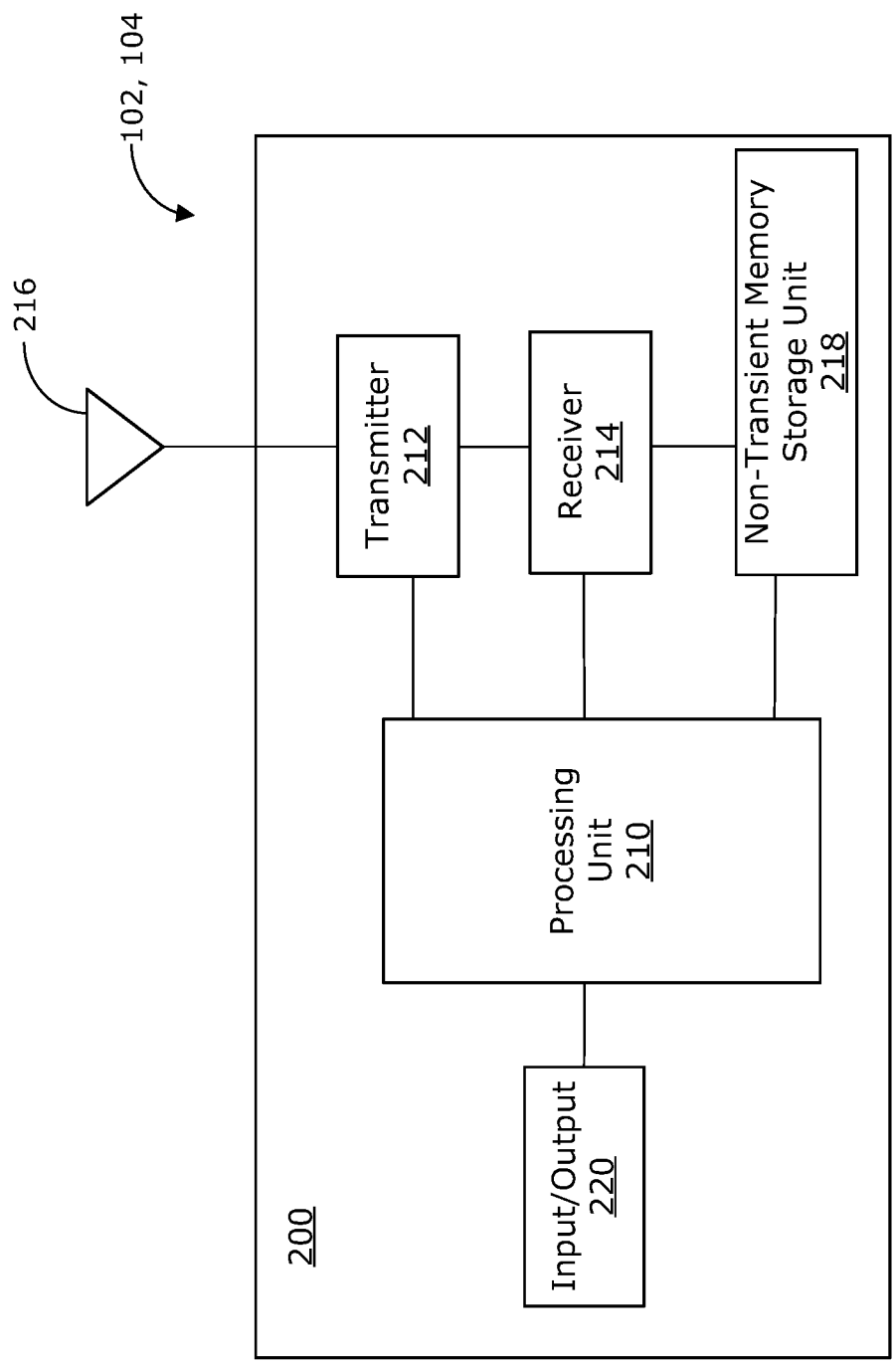
FIG. 2 illustrates an example wireless communication apparatus that may act as an AP 102 or an STA 104 shown in FIG. 1.

FIG. 2 shows an example wireless communication device 200 that may be used to implement an AP 102 or an STA 104 shown in FIG. 1. The wireless communication device 200 includes at least one processing unit 210, at least one transmitter 212, at least one receiver 214, one or more antennas 216, electronic storage including at least one non-transitory memory storage unit 218, and one or more input/output (I/O) devices or interfaces 220.

The processing unit 210 implements various processing operations of AP 102 or the receiving (target) STA 104, such as signal coding, data processing, power control, input/output processing, or any other functionality. The processing unit 210 can also be configured to implement some or all of the functionality and/or embodiments described herein. Each processing unit 210 includes any suitable processing or computing device configured to perform one or more operations. Each processing unit 210 can, for example, include a microprocessor, microcontroller, digital signal processor, field-programmable gate array, or application-specific integrated circuit. The processing unit 210 is operably connected to the I/O interfaces 220, transmitter 212 and receiver 214. The processing unit 210 may be configured to generate wireless signals based on signals received from input 220 for transmission by the transmitter 212 or to process wireless signals received from receiver 214. In some embodiments that communicate OFDM signals or OFDMA signals, the processing unit 210 may be configured to generate OFDM or OFDMA signals that are suitable for transmission by, for example, performing an inverse fast Fourier transform (IFFT) or any other suitable processing technique. The processing unit 210 may also be configured to process received OFDM signals or OFDMA signals by, for example, performing a Fast Fourier Transform (FFT) or any other suitable processing technique. In some embodiments, the processing unit 210 may be configured to detect the presence of an OFDM signal or OFDMA signal by performing a correlation or cross-correlation to detect a preamble. The preambles may be part of a predetermined frame structure for Wi-Fi communication. Although a single instance of a processing unit 210 is shown, it is understood that multiple instances of the processing unit 210 may be present in each wireless communication apparatus. For example, there may be at least one processing unit for processing output signals to be transmitted by the transmitter 212 and at least one processing unit for processing input signals from the receiver 214.

Transmitter 212 may include any suitable structure for generating signals for wireless or wired transmission. Each receiver 214 may include any suitable structure for processing signals received wirelessly or by wire. Each transmitter 212 and receiver 214 can include associated amplification and modulation/demodulation circuitry. Although shown as separate components, at least one transmitter 212 and at least one receiver 214 may be combined into a single transceiver. Each antenna 216 may include any suitable structure for transmitting and/or receiving wireless or wired signals. Although a common antenna 216 is shown here as being coupled to both the transmitter 212 and the receiver 214, one or more antennas 216 could be coupled to one or more transmitter(s) 212, and one or more separate antennas 216 could be coupled to one or more receiver(s) 214. In some examples, one or more antennas 216 may be an antenna array, which may be used for beamforming and beam steering operations. Each non-transitory memory storage unit 218 may include any suitable volatile and/or non-volatile storage and retrieval device(s). Any suitable type of memory may be used, such as random access memory (RAM), read-only memory (ROM), hard disk, optical disc, subscriber identity module (SIM) card, memory stick, secure digital (SD) memory card, and the like. The non-transitory memory storage unit 218 may store instructions and data used, generated, or collected by AP 102 or STA 104. For example, the non-transitory memory storage unit 218 could store software instructions or modules configured to implement some or all of the functionality and/or embodiments described herein and that are executed by the processing unit(s) 210.

The input/output device/interface 220 may permit interaction with a user or other devices in the network. The input/output device/interface 220 includes any suitable structure for providing information to or receiving/providing information from a user, including network interface communications.

In some embodiments, the AP 102 and STA 104 may be configured to communicate over various wireless channel bandwidths, including bandwidths having center frequencies of about 2.4 GHz, 5 GHz, 6 GHz, and bandwidths of 20 MHz, 40 MHz, or 80 MHz, 80+80 MHz, 160 MHz, 160+160 MHz, 320 MHz, 320+320 MHz, 480 MHz (such as 160+160+160 MHz), 640 MHz bandwidths. In some embodiments, the bandwidth of a channel less than 20 MHz may be used.

In the wireless network 100, the wireless communication apparatuses, such as AP 102 and STA 104, communicate with one another through various well-defined frame structures. The frame structures may be generated by the processing unit 210 of the wireless communication apparatus shown in FIG. 2. In some embodiments, a frame structure may be configurable to have the same bandwidth as a channel. The frame structure may be in the form of a PPDU, including a frame preamble portion and a payload portion. In some embodiments, there may be different types of PPDUs that may have different fields and different PHY layers and/or different MAC layers. For example, a single user (SU) PPDU, multiple-user (MU) PPDU, long-range (LR) SU PPDU, and Trigger-Based (TB) PPDU.

Figure 3:
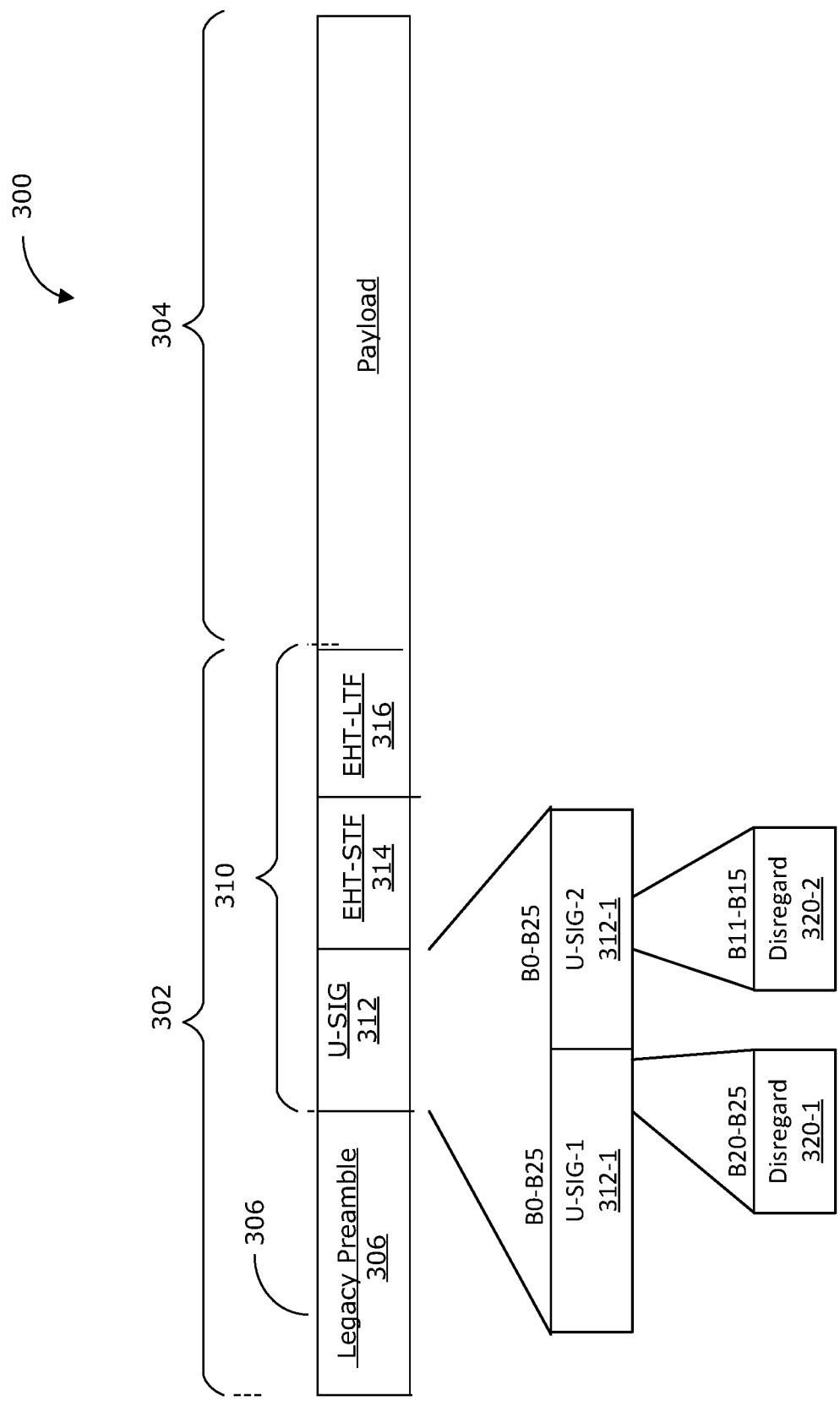
FIG. 3 illustrates an example of an EHT TB PPDU frame structure.

FIG. 3 illustrates an example of a frame structure for an EHT TB PPDU 300. The EHT TB PPDU 300 may be generated and transmitted by a transmitting wireless communication device 200 (e.g., STA 104) and received and decoded by a receiving wireless communication device 200 (e.g., AP 102). The EHT TB PPDU 300, which is a fame, is transmitted by one or more STAs 104 as a response to a trigger frame (TF) from an AP 102, and can include OFDMA uplink data from the one or more STAs 104. The TF transmitted by AP 102 enables the one or more STAs transmitting the EHT TB PPDU 300 to establish a synchronized transmission. The EHT TB PPDU 300 may include a preamble portion 302 followed by a payload portion 304.

As shown, the preamble portion 302 may include a legacy preamble portion 306 and an EHT preamble portion 310. The legacy preamble portion 306, which was first established in the IEEE 802.11a™ standard, may permit backward compatibility and coexistence with IEEE 802.11™ based devices. The legacy preamble portion 306 may include two OFDM symbols carrying a legacy short training field (L-STF) (not shown) and a legacy long training field (L-LTF) (not shown) configured for frame detection and receiver synchronization, respectively. The next OFDM symbol of the legacy preamble portion 306 may carry a legacy signal field (L-SIG) (not shown) that may contain rate and length values to hold off until the next transmission. The RL-SIG (not shown) may be used to support the coverage extension, such as 11ax. The legacy preamble portion 306 may be decoded by legacy Wi-Fi devices.

In the illustrated embodiment, the EHT preamble portion 310 includes U-SIG 312 field, EHT-STF 314 field, and EHT-LTF 316 field. Other fields such as L-STF, L-LTF, L-SIG, RL-SIG, U-SIG, and EHT-SIG fields may be referred to as pre-EHT modulated fields. The EHT-STF 314 and EHT-LTF 316, and payload 304 may be referred to as EHT modulated fields. An example of a proposed EHT Universal Signal (U-SIG) 312 field in the preamble of EHT TB PPDU is described for example in "11-20/1875r2, PDT PHY Update to Preamble U-SIG, IEEE 802.11be, November 2020", incorporated herein by reference. The U-SIG 312 field carries information to interpret the EHT TB PPDU. The purpose of the U-SIG 312 field is to bring forward compatibility to the EHT preamble to be compatible with future 802.11 generations.

In some embodiments, the frame formats of the 11be standard and beyond will use a two-OFDM-symbol long universal SIG (U-SIG) 312, which may comprise information bits regarding the payload portion 304. As it may be appreciated, being two symbols long, the U-SIG 312 may possess a maximum bit carrying capacity of 42 bits. The U-SIG 312 may have version-independent information followed by version-dependent information. The version-independent information is for compatibility across 802.11 generations. This version-independent information is consistent in location and interpretation across various 802.11 generations. For instance, the PHY version identifier is a piece of the version-independent information. The version-independent information of U-SIG 312 of EHT TB PPDU may include two parts, U-SIG-1 (312-1) and U-SIG-2 (312-2)), each of which is 26 bits in length. U-SIG-1 (312-1) may include a three-bit PHY format identifier, a three-bit bandwidth information (not shown), and a one-bit UL/DL flag (not shown). It may also include a Basic Service Set (BSS) color of 6 bits (not shown), transmission (TX) opportunity (TXOP) duration of 7 bits (not shown), and 5 disregard bits 320-1. U-SIG-2 (312-2) may include 2 bits for PPDU type and compression used (not shown), 1 bit for validation (not shown), and 2 subfields with 4 bits each for spatial reuse to indicate whether specific reuse modes are allowed (not shown). U-SIG-2 312-2 also includes 5 disregard bits 320-2 and other bits for cyclic redundancy check (CRC) (not shown) and tail bits (not shown).

Therefore, the U-SIG 312 of the EHT TB PPDU includes two separate disregard subfields 320-1, 320-2, namely bits B20-25 of U-SIG-1 312-1 and bits B11-15 of U-SIG-2 312-1. The content of these 6 bits and 5 bits, respectively, is copied from the TF received from AP 102. The present disclosure provides a TF structure that enables the bits whose content is copied into the disregard bits to be defined. This can enable the disregard bits to be used efficiently in subsequent 802.11 generations.

The version-dependent information of U-SIG 312 may include the number of EHT long training fields symbols, a mid-amble periodicity subfield, and a space-time block coding flag, among other information. Further, the presence of the U-SIG 312, together with other symbols, such as L-SIG, may allow the receiver to differentiate between frames formats relating to different standard amendments, for example between an 11be frame and an 11ax frame. For example, for 11be EHT transmission, an L_LENGTH field, which is a field in L-SIG may be set such that value of L_LENGTH modulo 3 is equal to 1, and the bit B0 of U-SIG 312 may be set to 0, which the receiver may recognize as an EHT PPDU.

In some example embodiments, the EHT short training field (STF) 314 and EHT long training field (LTF) 316 may follow the U-SIG 312 field and define the time and frequency tuning of MIMO/OFDMA. In some embodiments, EHT-STF 314 and EHT-LTF 316 are of longer variants of STF and LTF from the 11ax standard, which may enable extended range and better channel estimation. In some of the wide BW embodiments having channel BW of 80 MHz or greater, the EHT-STF 314 field and the EHT-LTF 316 field are repeated every 20 MHz. In some embodiments, the phase of every 20 MHz copy of the EHT-STF 314 and EHT-LTF 316 may be rotated to reduce the peak-to-average power ratio and enhance correlation performance.

The payload portion 304 may include one or more fields in the form of OFDM symbols containing Physical Layer Convergence Protocol (PLCP) Service Data Units (PSDU), which are the data units sent down from the MAC layer for transmission on the wireless medium.

Figure 4:
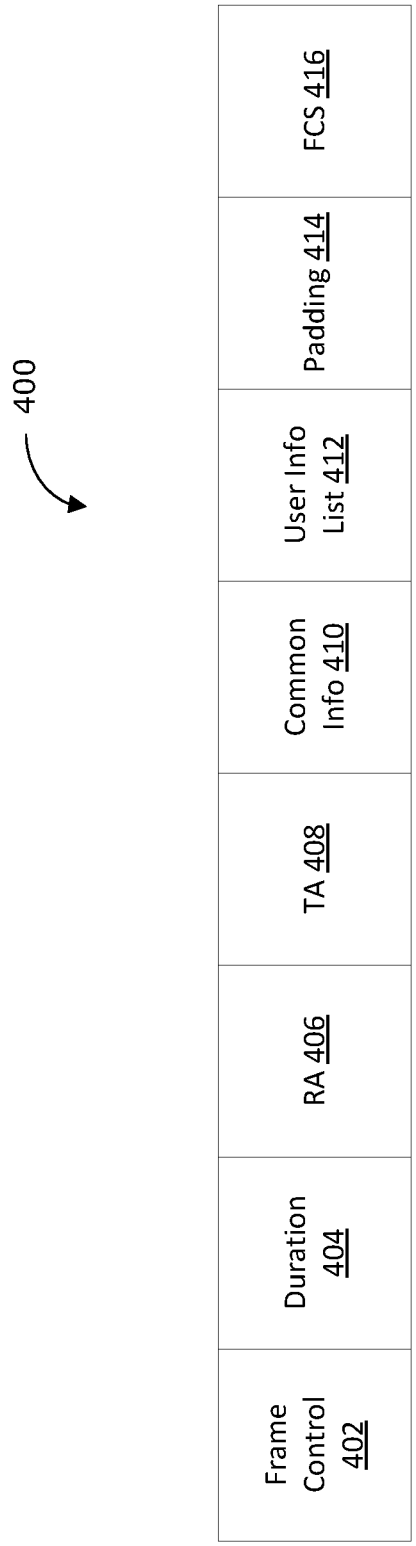

FIG. 4 is an example of a trigger frame 400 format based on the TF format of 802.11ax. Although reference is made to 802.11ax, it is noted that techniques or mechanisms according to some implementations of the present disclosure can be used in conjunction with other standards, including future generations of the IEEE 802.11™ standards (e.g. 802.11be and beyond) or different standards. The purpose of the trigger frame 400 is to trigger target STAs 104 to respond to a received frame. The trigger frame 400 is sent by the AP 102 to one or more STAs 104 and triggers the one or more STAs 104 to transmit an EHT TB PPDU 300.

Subfields of the trigger frame 400 include a frame control 402 containing header information, a protocol version, a type and subtype of the frame, and other parameters. The frame control 402 is allocated 2 octets. Further, the duration field 404 is also allocated 2 octets, and it sets the duration of the frame. Six octets are allocated for RA 406, and 6 octets are allocated for TA 408. These fields set the addresses of the receiving and transmitting STAs 104, respectively. The common info field 410, allocated at least 8 octets, may inform the STAs 104 of the frame structure and setup. The user info list 412 consists of information for every STA 104 receiving the EHT TB PPDU frames. The trigger frame may also include a variable number of octets for a user info list 412, allowing it to identify every STA 104 receiving the EHT TB PPDU frames. Additionally, a variable number of octets are reserved for padding 414 to satisfy processing-time constraints required by the STAs 104. Lastly, four octets are allocated for a frame check sequence (FCS) for the error-detecting code added to the frame.

Figure 5:
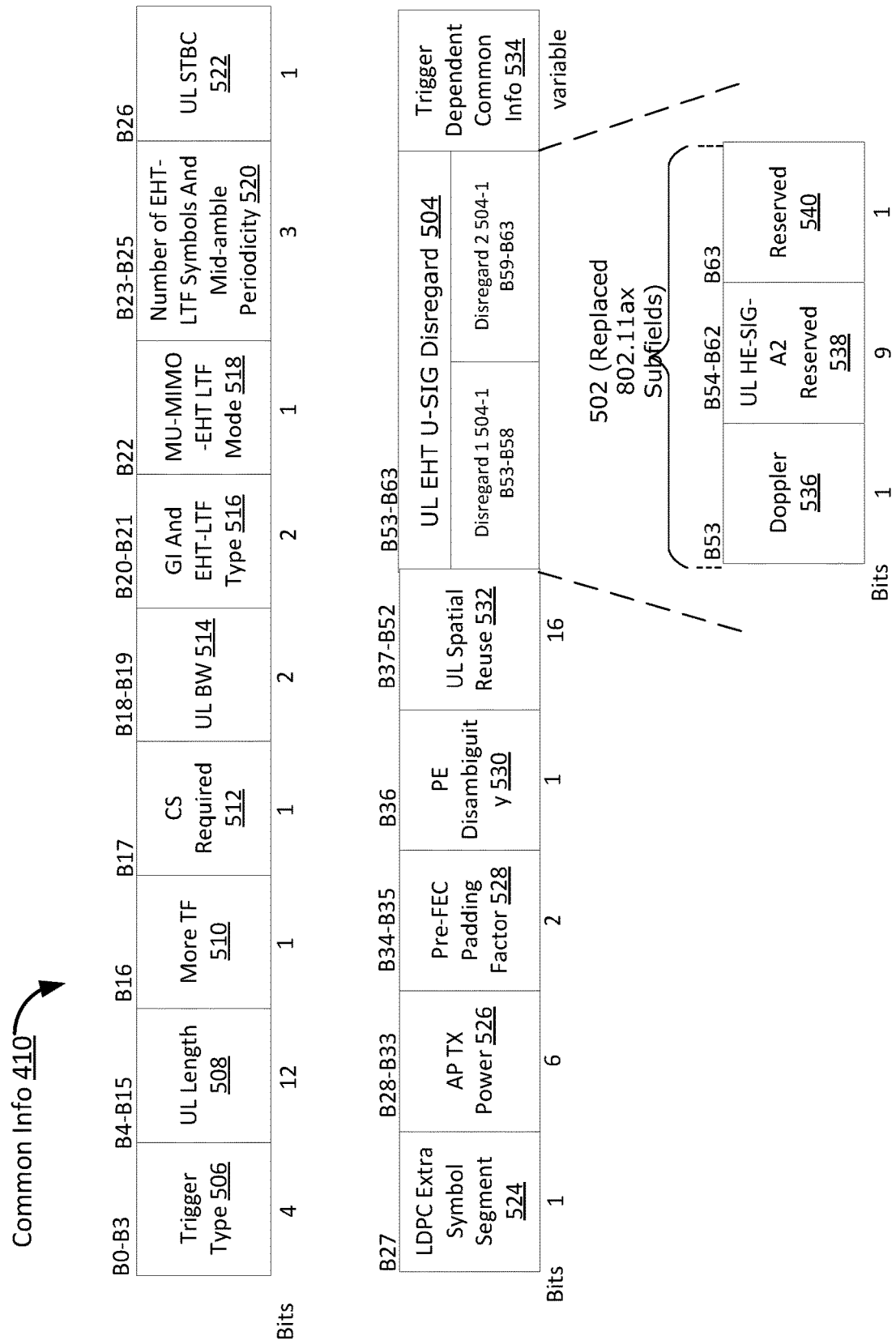
FIG. 5 illustrates an example using the common info field of the trigger frame to define UL EHT U-SIG Disregard.

FIG. 5 illustrates the content of a common info field 410 of trigger frame 400, including a UL EHT-SIG Disregard 504 subfield according to an example embodiment of the present disclosure. The UL EHT-SIG Disregard 504 subfield may carry EHT related information such as the STAs' 320 MHz bandwidth, 16 spatial stream information, and Aggregated PPDU related information.

The common info field 410 may include the following subfields: trigger type 506, which may carry information relates to the trigger frame 400 variant as being basic, beamforming report poll, multiuser request to send (MU-RTS), bandwidth query report poll BQRP, etc.; subfield UL length 508 may indicate the expected response frame's length; More TF 510 subfield may indicate target wake time or power save; CS required 512 may indicate whether the target STAs 104 are required to consider the network allocation vector (NAV) to decide whether to respond to a received frame; UL BW 514 may indicate the transmission's bandwidth; GI and LTF type 516 may provide information about the guard interval and long training field (LTF) used for the transmission (guard interval corresponds to the space between symbols transmitted, LTF may provide information on channel estimation to recover data; MU-MIMO HW-LTF Mode 518 subfield may specify whether the LTF sequence is masked by an orthogonal code; and number of EHT-LTF (EHT Long Training Field) symbols and mid-amble periodicity 520 may indicate the number of EHT-LTF symbols present in the EHT TB PPDU response.

Further, the UL STBC 522 subfield may be set to indicate the use of uplink space-time block coding; LDPC extra symbol segment 524 may indicate the LDPC extra symbol segment's value in the trigger frame 400; AP TX power 526 may indicate the power used to transmit the frame when the AP sends the trigger frame; pre-FEC padding factor 528 may contain information related to the MAC and PHY operation (this padding process may be conducted before performing forward error correction (FEC) coding); PE disambiguity 530 may specify the packet extension (PE) information; and trigger dependent common info 534 may be an optional subfield part of the trigger frame format.

In example embodiments, bits B53-B63 of the trigger frame's common info field 410 are allocated as a UL EHT U-SIG Disregard 504 subfield. These 11 bit locations can be used to specify the 11 bits of information that are to be copied into the 6 Bit and 5 Bit disregard subfields 320-1, 320-2 of U-SIG-1 312-1 and U-SIG-2 312-2, respectively, of the EHT TB PPDU 300. In this regard, it will be noted that the UL EHT U-SIG Disregard 504 subfield replaces a number of subfields that were located in the trigger frame format of 802.11ax. In FIG. 5, the replaced subfields are indicated by block 502.

Subfields of block 502 of 802.11ax are not required for the following reasons. In 802.11ax, Doppler 536 subfield may indicate if mid-ambles exist in the packet. If the packet is not larger than the mid-amble, then the channel may be time-varying. The term mid-amble is a reference location for the middle of the packet. However, the Doppler 536 subfield is not used in U-SIG 312 of EHT TB PPDU. Further, in 802.11ax, the UL HE-SIG-A2 Reserved subfield 538 may carry values to be included in the reserved field of the HE-SIG-A2 of the HE TB PPDU. However, such a field will not be required in the context of EHT TB PPDU. Lastly, there is a reserved bit subfield 540.

Thus, in the illustrated example, the UL EHT U-SIG Disregard 504 subfield, with a size of 11 bits, may occupy locations B53-B63 of the common info field 410. The content of the UL EHT U-SIG Disregard 504 subfield is copied into the non-transitory memory storage unit 218 of the receiving STA 104. The receiving STA 104, subsequently copies the content of the 11 bit UL EHT U-SIG Disregard 504 subfield into the U-SIG 11 disregard bits of the EHT TB PPDU 300, therefore, defining the bits the U-SIG disregard bits are copied from. In particular, the receiving STA 104 may copy the content of UL EHT U-SIG Disregard 504 subfield into B20-25 of U-SIG-1 and B11-15 of U-SIG-2 of the EHT TB PPDU.

The 11 bit UL EHT U-SIG Disregard 504 subfield may be considered as two subfields, namely a 6-bit UL EHT U-SIG Disregard 1 subfield 504-1 (Bits B53 to B58) that includes bits to be copied into the disregard subfield 320-1 of EHT TB PPDU 300, and 5-bit UL EHT U-SIG Disregard 2 subfield 504-2 (Bits B59 to B63) that includes bits to be copied into the disregard subfield 320-2 of EHT TB PPDU 300, in accordance with an example embodiment of the present disclosure.

Figure 6:
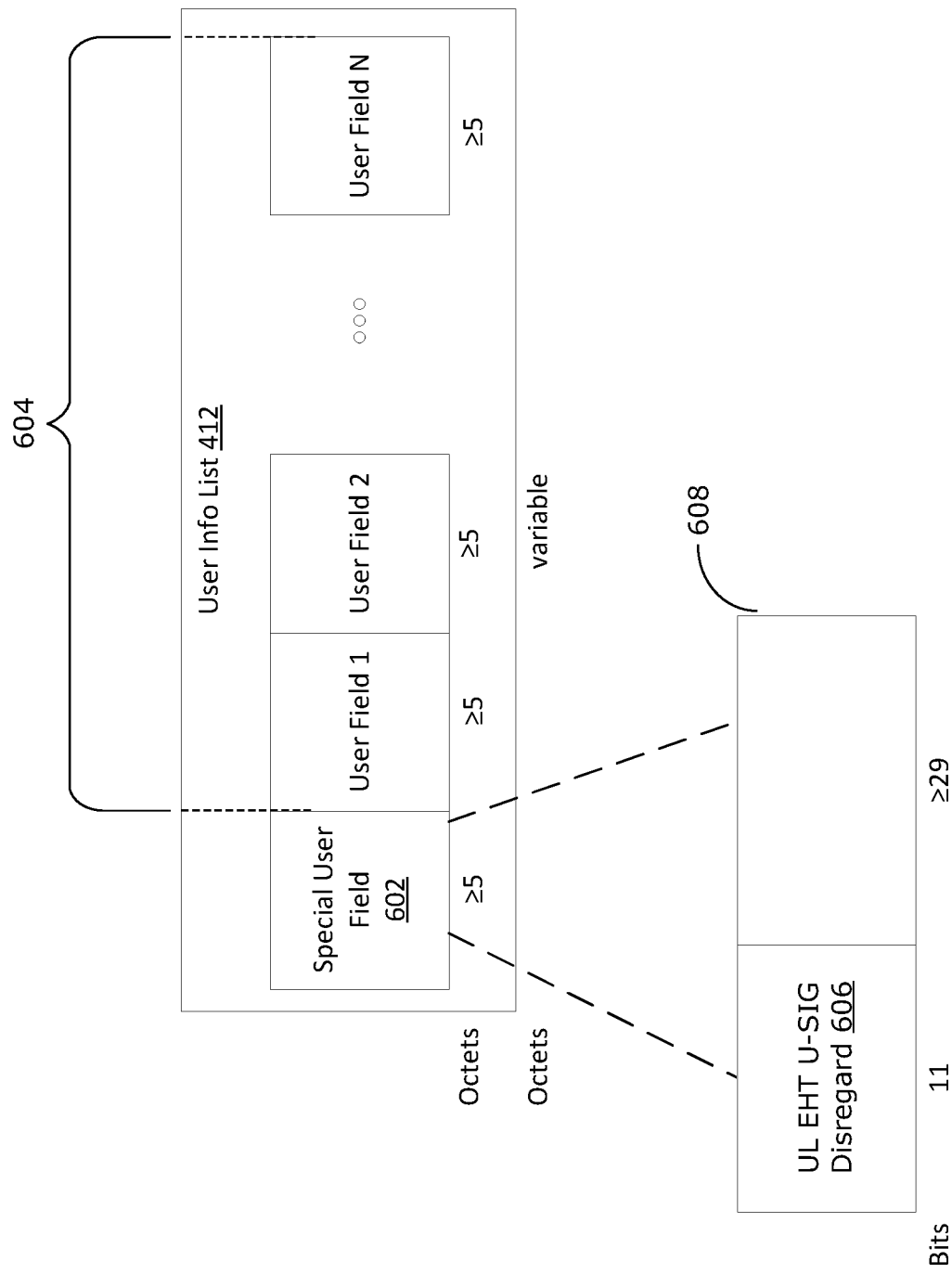
FIG. 6 illustrates an example using the user info list field of the trigger frame to define UL EHT U-SIG Disregard.

FIG. 6 presents a block diagram of an alternative example for providing a UL EHT U-SIG disregard subfield in the trigger frame 400. In the example of FIG. 6, instead of using bits B53 to B63 of the common info field 410 as illustrated in FIG. 5, an UL EHT U-SIG disregard 606 subfield is instead added into a special user field 602 that is prepended to the user fields that are included in the user info list 412 of trigger frame 400. Accordingly, space in the user info list 412 of the trigger frame 400 is used for the 11 disregard bits of U-SIG 312 of the EHT TB PPDU 300 to be copied from. The user info list 412 may contain information of the target STAs 104 such as identification, modulation and coding scheme, forward error correction coding type, etc. The size of user info list 412 is variable depending on the number of STAs 104. Each STA 104 corresponds to one of the user fields, i.e. user field 1, user field 2, ... as shown at 604. Since the user info list's size is variable, an extra user field is created, named special user field 602. As a result, the total number of user fields is increased by 1 to a total of N+1 user fields. Each user field is allocated at least 40 bits. The 11-bit UL EHT U-SIG Disregard 606 subfield occupies 11 bits of the at least 40 bits of the special user field 602. The other bits of at least 29 bits in block 608 may be used to convey additional information.

FIG. 6 shows UL EHT U-SIG Disregard 606 subfield occupying the first 11 bits of the special user field 602, but it is to be understood that UL EHT U-SIG Disregard 606 subfield may occupy any 11 bits, contiguous or not, of the at least 40 bits allocated for the special user field. The UL EHT U-SIG Disregard 606 subfield is copied into the non-transitory memory storage unit 218 of the receiving STA 104, and the STA 104 copies its content into the disregard bits of the U-SIG of the EHT TB PPDU.

Figure 7:
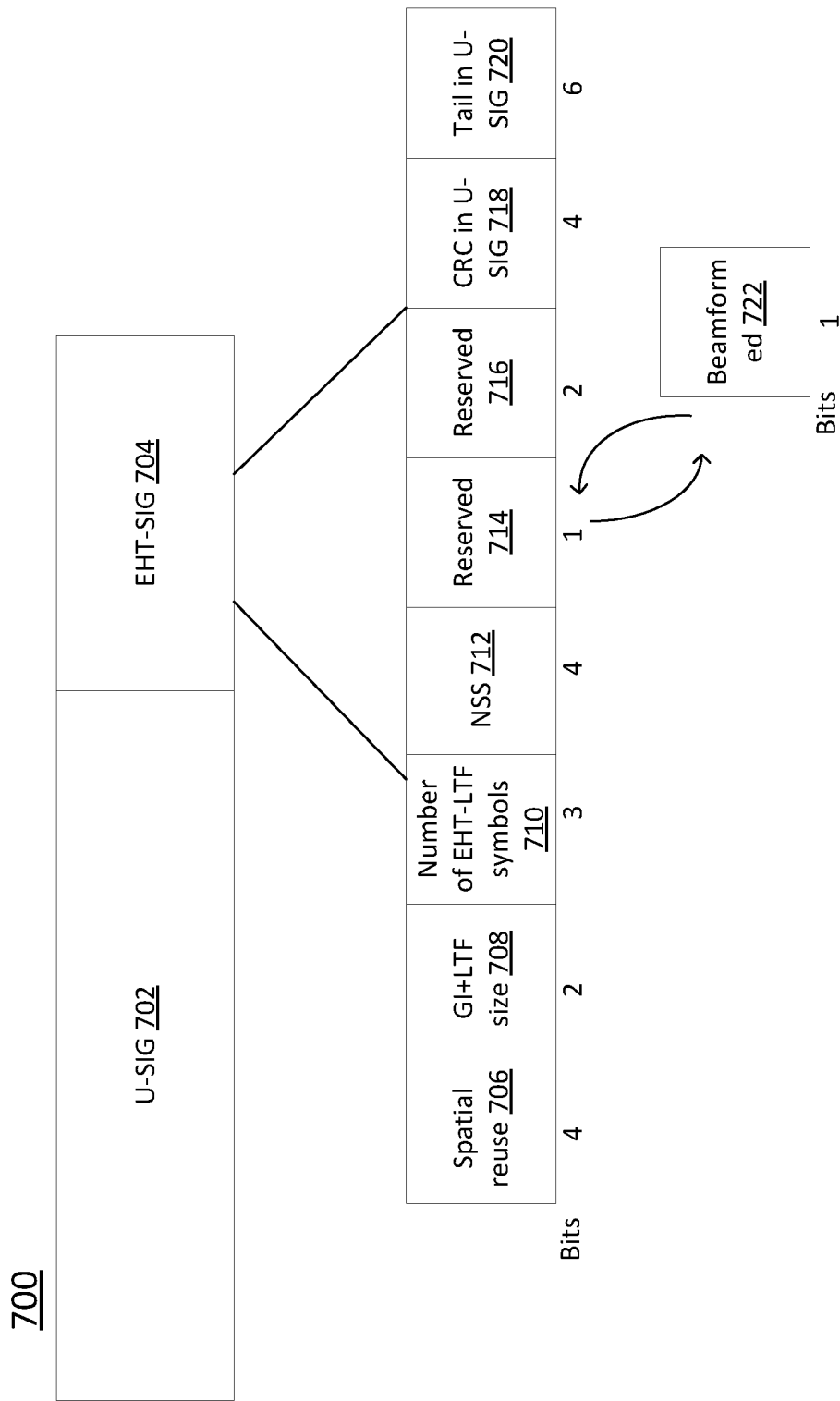
FIG. 7 illustrates an example of the EHT NDP PPDU frame format after releasing the beamformed bit.

FIG. 7 is a block diagram of an EHT NDP frame 700 according to an example embodiment of the present disclosure. The EHT NDP frame 700 may consist of U-SIG field 702 and EHT-SIG field 704. The U-SIG field 702 may include at least version-independent information and version-dependent information. The EHT-SIG field 704 may include a spatial reuse subfield 706 to increase parallel transmissions. The spatial reuse subfield 706 may indicate whether spatial reuse modes are allowed while transmitting an EHT NDP frame format. Other subfields of the EHT-SIG field 704 may include: GI and LTF size 708, which may provide information about the guard interval and long training field (LTF) used for transmission; number of EHT LTF symbols 710; number of spatial stream streams (NSS) 712, two reserved subfields 714 (1 Bit), 716 (2 Bits); cyclic redundancy check (CRC) subfield 718; and tail subfield 720.

In a previously proposed EHT-SIG structure, as set out in "11-20/1317r3, SIG contents discussion for EHT sounding NDP, IEEE 802.11be, November 2020", disclosed herein in its entirety by reference, the reserved subfield 714 is instead designated as a beamformed subfield 722 that may be used to instruct a receiver to run a smoothing operation for channel estimation. However, the smoothing operation can be performed regardless of the value of the beamformed subfield 722 since the EHT NDP frame 700 is never beamformed. The beamformed subfield 722 is, therefore, redundant. This example embodiment releases the beamformed subfield 722 and reserves the bit for other purposes, creating a reserved subfield 714. Some of the purposes may include increasing bandwidth or spatial stream for future amendments.

Through the descriptions of the preceding embodiments, the present invention may be implemented by using hardware only, or by using software and a necessary universal hardware platform, or by a combination of hardware and software. Based on such understandings, the technical solution of the present invention may be embodied in the form of a software product. The software product may be stored in a non-volatile or non-transitory storage medium, which can be a compact disk read-only memory (CD-ROM), USB flash drive, or a hard disk. The software product includes a number of instructions that enable a computer device (personal computer, server, or network device) to execute the methods provided in the embodiments of the present invention.

Although the present invention and its advantages have been described in detail, it should be understood that various changes, substitutions and alterations can be made herein without departing from the invention as defined by the appended claims.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method for transmitting data in a wireless local area network (WLAN), comprising:
   transmitting, in the WLAN, a trigger frame from a first wireless communication device, the trigger frame comprising one or more U-Sig-Disregard subfields of bits totaling 11 bits at predefined bit locations within the trigger frame that are populated with values for a second wireless communication device to copy into an 11-bit U-Sig-Disregard field of a trigger based frame for transmission to the first wireless communication device.

2. The method of claim 1, wherein the trigger frame has a common information field, the common information field having the one or more U-Sig-Disregard subfields of bits.

3. The method of claim 2, wherein the common information field has at least 63 bits and the one or more U-Sig-Disregard subfields of bits are included in bit locations 53 to 63.

4. The method of claim 1, wherein the trigger frame includes a user information field, the user information field having the one or more U-Sig-Disregard subfields of bits.

5. The method of claim 4, wherein the one or more U-Sig-Disregard subfields of bits are 11 bits included within 5 octets of bits at a beginning of the user information field.

6. The method of claim 4, wherein the one or more U-Sig-Disregard subfields of bits are 11 bits of the user information field, the 11 bits being contiguous or non-contiguous.

7. A method for transmitting data in a wireless local area network (WLAN), comprising:
   receiving, by a station (STA) in the WLAN, a trigger frame, and in response to the trigger frame:
   copying content from 11 predefined bit locations of the trigger frame corresponding to one or more U-Sig-Disregard subfields of bits into 11 predefined U-Sig-Disregard field bit locations of a response frame; and
   transmitting, by the STA, the response frame.

8. The method of claim 7, wherein the 11 predefined U-Sig-Disregard field bit locations of the response frame are locations B20 to B25 of a universal signal 1 (U-SIG-1) subfield and B11 to B15 of a universal signal 2 (U-SIG-2) subfield of a universal signal (U-SIG) field of an EHT trigger based (TB) physical layer protocol data unit (PPDU).

9. The method of claim 7, wherein the 11 predefined U-Sig-Disregard field bit locations of the trigger frame comprise 11 bits determined from a user info list field of the trigger frame, the 11 bits being 11 contiguous bits.

10. The method of claim 7, wherein the 11 predefined U-Sig-Disregard field bit locations of the trigger frame comprise 11 bits determined from a user info list field of the trigger frame, the 11 bits being non-contiguous bits.

11. A wireless communication device for transmitting data in a wireless local area network (WLAN), the wireless communication device comprising:
   a processor;
   a memory coupled to the processor, the memory tangibly storing thereon executable instructions that, when executed by the processor, cause the wireless communication device to:
   transmit, in the WLAN, a trigger frame from a first wireless communication device, the trigger frame comprising one or more U-Sig-Disregard subfields of bits totaling 11 bits at predefined bit locations within the trigger frame that are populated with values for a second wireless communication device to copy into an 11-bit U-Sig-Disregard field of a trigger based frame for transmission to the first wireless communication device.

12. The device of claim 11, wherein the trigger frame has a common information field, the common information field having the one or more U-Sig-Disregard subfields of bits.

13. The device of claim 12, wherein the common information field has at least 63 bits and the one or more U-Sig-Disregard subfields of bits are included in bit locations 53 to 63.

14. The device of claim 11, wherein the trigger frame includes a user information field, the user information field having the one or more U-Sig-Disregard subfields of bits.

15. The device of claim 14, wherein the one or more U-Sig-Disregard subfields of bits are 11 bits included within 5 octets of bits at a beginning of the user information field.

16. The device of claim 14, wherein the one or more U-Sig-Disregard subfields of bits are 11 bits of the user information field, the 11 bits being contiguous or non-contiguous.

17. A wireless communication device for transmitting data in a wireless local area network (WLAN), the wireless communication device comprising:
   a processor;
   a memory coupled to the processor, the memory tangibly storing thereon executable instructions that, when executed by the processor, cause the wireless communication device to:
   receive a trigger frame, and in response to the trigger frame:
   copy content from 11 predefined bit locations of the trigger frame corresponding to one or more U-Sig-Disregard subfields of bits into 11 predefined U-Sig-Disregard field bit locations of a response frame; and
   transmit the response frame.

18. The device of claim 17, wherein the 11 predefined U-Sig-Disregard field bit locations of the response frame are locations B20 to B25 of a universal signal 1 (U-SIG- 1) subfield and B11 to B15 of a universal signal 2 (U-SIG-2) subfield of a universal signal (U-SIG) field of an EHT trigger based (TB) physical layer protocol data unit (PPDU).

19. The device of claim 17, wherein the 11 predefined U-Sig-Disregard field bit locations of the trigger frame comprise 11 bits determined from a user info list field of the trigger frame, the 11 bits being 11 contiguous bits.

20. The device of claim 17, wherein the 11 predefined U-Sig-Disregard field bit locations of the trigger frame comprise 11 bits determined from a user info list field of the trigger frame, the 11 bits being non-contiguous bits.

* * * * *